(12) United States Patent
Tajima

(10) Patent No.: US 11,376,598 B2
(45) Date of Patent: Jul. 5, 2022

(54) CARTRIDGE FOR NUCLEIC ACID DETECTION

(71) Applicant: UNIVERSAL BIO RESEARCH CO., LTD., Chiba (JP)

(72) Inventor: Hideji Tajima, Chiba (JP)

(73) Assignee: UNIVERSAL BIO RESEARCH CO., LTD., Chiba (JP)

(*) Notice: Subject to any disclaimer, the term of this patent is extended or adjusted under 35 U.S.C. 154(b) by 179 days.

(21) Appl. No.: 16/610,797

(22) PCT Filed: May 10, 2018

(86) PCT No.: PCT/JP2018/018138
§ 371 (c)(1),
(2) Date: Nov. 4, 2019

(87) PCT Pub. No.: WO2018/207875
PCT Pub. Date: Nov. 15, 2018

(65) Prior Publication Data
US 2020/0061609 A1 Feb. 27, 2020

(30) Foreign Application Priority Data
May 12, 2017 (JP) .............................. JP2017-095410

(51) Int. Cl.
*B01L 3/00* (2006.01)
*B01L 7/00* (2006.01)
*C12Q 1/686* (2018.01)

(52) U.S. Cl.
CPC ............. *B01L 3/50851* (2013.01); *B01L 7/52* (2013.01); *B01L 2200/16* (2013.01);
(Continued)

(58) Field of Classification Search
None
See application file for complete search history.

(56) References Cited

U.S. PATENT DOCUMENTS 6,079,593 A * 6/2000 Konrad ................... B01L 9/543
206/499
2001/0041341 A1* 11/2001 Besemer ........... B01L 3/502707
435/6.1
(Continued)

FOREIGN PATENT DOCUMENTS

JP   H11316226    11/1999
JP   2006-125868   5/2006
(Continued)

OTHER PUBLICATIONS

Extended European Search Report in connection to European Patent Application No. 18799135.1, dated Dec. 10, 2020.
(Continued)

*Primary Examiner* — Matthew D Krcha
(74) *Attorney, Agent, or Firm* — Meunier Carlin & Curfman LLC

(57) ABSTRACT

A cartridge 100 for nucleic acid detection is provided with: a first member 110 having multiple nucleic acid extraction wells; a second member 120 having a nucleic acid amplification and determination well for amplification of a nucleic acid and detection of the amplified nucleic acid; and multiple reagent containers 130. The multiple reagent containers 130 are fixed between the first member 110 and the second member 120.

19 Claims, 15 Drawing Sheets

US 11,376,598 B2
Page 2

(52) U.S. Cl.
CPC . *B01L 2300/041* (2013.01); *B01L 2300/0832* (2013.01); *B01L 2300/12* (2013.01); *B01L 2300/1805* (2013.01); *C12Q 1/686* (2013.01)

(56) References Cited

U.S. PATENT DOCUMENTS

| | | | |
|---|---|---|---|
| 2010/0209304 A1* | 8/2010 | Sarofim | B01L 3/502707 422/503 |
| 2011/0181875 A1* | 7/2011 | Nakahana | B01L 3/5453 356/246 |
| 2014/0048540 A1 | 2/2014 | Tajima | |
| 2014/0051083 A1 | 2/2014 | Tajima | |
| 2014/0206088 A1* | 7/2014 | Lentz | B01L 3/50853 436/54 |
| 2014/0260118 A1 | 9/2014 | Knight | |
| 2014/0263153 A1 | 9/2014 | Knight | |
| 2014/0271360 A1 | 9/2014 | Buse et al. | |
| 2014/0271409 A1 | 9/2014 | Knight et al. | |
| 2014/0272989 A1 | 9/2014 | Knight | |
| 2015/0108034 A1* | 4/2015 | Deutschle | A61J 1/16 206/562 |
| 2015/0315630 A1 | 11/2015 | Tajima | |
| 2015/0362515 A1 | 12/2015 | Buse et al. | |
| 2015/0369835 A1 | 12/2015 | Knight et al. | |
| 2016/0008810 A1 | 1/2016 | Knight | |
| 2016/0023211 A1 | 1/2016 | Knight | |
| 2016/0025722 A1 | 1/2016 | Tajima | |
| 2016/0114318 A1 | 4/2016 | Knight | |
| 2016/0129437 A1* | 5/2016 | Kayyem | B01L 3/502 204/600 |
| 2017/0065972 A1 | 3/2017 | Knight | |
| 2017/0153264 A1 | 6/2017 | Buse et al. | |
| 2017/0160196 A1 | 6/2017 | Tajima et al. | |
| 2017/0259258 A1 | 9/2017 | Buse et al. | |
| 2017/0341073 A1 | 11/2017 | Knight | |
| 2018/0361376 A1 | 12/2018 | Knight | |
| 2019/0001324 A1 | 1/2019 | Knight | |
| 2019/0134626 A1 | 5/2019 | Knight | |
| 2019/0137397 A1 | 5/2019 | Tajima | |

FOREIGN PATENT DOCUMENTS

| | | |
|---|---|---|
| JP | 2016-144445 | 8/2016 |
| JP | 2017-72616 A | 4/2017 |
| WO | 2009/054870 | 4/2009 |

OTHER PUBLICATIONS

International Search Report (English) and Written Opinion dated Jul. 31, 2018, from International Application No. PCT/JP2018/018138, 9 pages.

Uehara, M., "Development of a novel and rapid fully automated genetic testing system", Analytical Sciences, 2016, vol. 32, p. 1375-1379.

* cited by examiner

CARTRIDGE FOR NUCLEIC ACID DETECTION

TECHNICAL FIELD

The present invention relates to a cartridge for extracting and detecting a biological matter. More particularly, the present invention relates to a cartridge for nucleic acid detection which can be used for conducting nucleic acid extraction, amplification and detection.

BACKGROUND ART

In order to automatically detect a biological matter by an immunoassay, cartridges such as those described in Patent documents 1 and 2 have conventionally been employed. In recent years, cartridges prefilled with a DNA extraction reagent and the like have been provided for extracting DNA for PCR.

However, there has been difficulty in integrating such cartridges into one cartridge for conducting DNA extraction, PCR amplification and determination of the amplified DNA all the way through in one cartridge since the production process and the specification as product members differ in accordance with the characteristics of the reagents used for the respective treatments and the requirements such as the conditions employed for determination. The specification that renders integration difficult may presumably include (A) selection of reagents used for extracting DNA from a specimen (lysis buffer, wash buffer, etc.), (B) selection of PCR reagents (Master Mix, primer, buffer, etc.) and (C) arrangement of wells used for determination while performing PCR.

Since PCR reagents do not allow even a slight contamination, for example, (i) DNA polymerase, (ii) constituents of a DNA sequence such as a DNA primer, (iii) a lysis buffer, and the like each need to be prepared in a completely isolated chamber, lyophilized and sealed in a container with an aluminum seal. The sealed containers are transferred to an assembly chamber to be provided together as a PCR kit.

Accordingly, even though a technique for automatically mixing the reagents (i), (ii) and (iii) and else can be established, the reagents (i), (ii) and (iii) and else had to be provided as a kit of separate cartridges/wells.

PRIOR ART DOCUMENTS

Patent Documents

Patent document 1: Japanese Unexamined Patent Application Publication No. Heisei 11-316226
Patent document 2: Japanese Unexamined Patent Application Publication No. 2006-125868

SUMMARY OF INVENTION

Problem to be Solved by Invention

The present invention has an objective of providing a cartridge for nucleic acid detection, which has a novel structure in that all of the reagents used for extracting, amplifying and determining nucleic acids are sealed therein. Alternatively, the present invention has an objective of providing a cartridge for nucleic acid detection whose structure can be altered according to the characteristics of the reagents and the requirements such as the conditions employed for determination. Alternatively, the present invention has an objective of providing a cartridge for nucleic acid detection which has all of the reagents used for extracting, amplifying and determining nucleic acids sealed therein while reducing the risk of contaminating each of these reagents.

Means for Solving Problem

The aspects of the present invention are as follows.
(Aspect 1)
A cartridge for nucleic acid detection which is used in an apparatus for extracting nucleic acids from a specimen, amplifying the extracted nucleic acids and detecting the amplified nucleic acids, the cartridge comprising:
a first member provided with a plurality of nucleic acid extraction wells, the first member comprising at least one nucleic acid extraction well having at least one nucleic acid extraction reagent sealed therein in advance;
a second member provided with a nucleic acid amplification/determination well for amplifying the nucleic acids and determining the amplified nucleic acids; and
one or a plurality of reagent containers having one or a plurality of nucleic acid amplification reagents sealed therein in advance,
wherein the one or the plurality of reagent containers are fixed to be a part of the first member and/or the second member to integrate the first member, the second member and the plurality of reagent containers.
(Aspect 2)
The cartridge for nucleic acid detection according to Aspect 1, wherein the cartridge for nucleic acid detection is fixed to the first member and the second member by being sandwiched between the first member and the second member.
(Aspect 3)
The cartridge for nucleic acid detection according to either one of Aspects 1 and 2, wherein the plurality of nucleic acid amplification reagent containers are fitted into first openings formed in the first member and/or second openings formed in the second member.
(Aspect 4)
The cartridge for nucleic acid detection according to Aspect 3, wherein:
the first member is provided with a first top plate that has a plurality of open nucleic acid extraction wells and an attachment plate having the first openings;
the second member is provided with a second top plate that has the second openings; and
the second top plate is attached to the attachment plate.
(Aspect 5)
The cartridge for nucleic acid detection according to either one of Aspects 3 and 4, wherein: a protrusion is formed on the inner surface of the first opening or the second opening; the container is provided with a flange that protrudes out from the outer surface of the container; and the flange sits on the protrusion.
(Aspect 6)
The cartridge for nucleic acid detection according to Aspect 5, wherein the protrusion is an annular protrusion; and the flange is an annular flange.
(Aspect 7)
The cartridge for nucleic acid detection according to any one of Aspects 1-6, wherein a plurality of recessed parts are formed in either one of the first member or the second member while a plurality of nails are formed in the other one of the first member or the second member so that the plurality of nails can lock with the plurality of recessed parts to integrate the first member, the second member and the plurality of reagent containers.

(Aspect 8)
The cartridge for nucleic acid detection according to any one of Aspects 1-7, wherein the first member and the second member are welded.

(Aspect 9)
The cartridge for nucleic acid detection according to any one of Aspects 1-8, comprising a plurality of suction parts that can be suctioned by a cartridge picker.

(Aspect 10)
The cartridge for nucleic acid detection according to Aspect 9, wherein the plurality of suction parts are hollows formed in each of the first member and the second member.

(Aspect 11)
The cartridge for nucleic acid detection according to any one of Aspects 1-10, wherein the first member is provided with a heating well for heating and denaturing the extracted nucleic acids.

(Aspect 12)
The cartridge for nucleic acid detection according to any one of Aspects 1-11, wherein the container is provided with an opening, a seal for sealing the opening, and a container information storage medium formed on the seal.

(Aspect 13)
The cartridge for nucleic acid detection according to any one of Aspects 1-14, wherein the first member is provided with a plurality of ribs along its longitudinal direction.

(Aspect 14)
The cartridge for nucleic acid detection according to any one of Aspects 1-16, wherein the second member is provided with a plurality of ribs along its longitudinal direction.

(Aspect 15)
The cartridge for nucleic acid detection according to any one of Aspects 1-16, wherein the nucleic acid amplification/determination well is fitted into the second member without being tightly fixed thereto.

(Aspect 16)
A cartridge for nucleic acid detection which is used in an apparatus for extracting nucleic acids from a specimen, amplifying the extracted nucleic acids and detecting the amplified nucleic acids, wherein a base member of the cartridge for nucleic acid detection comprises:
a plurality of nucleic acid extraction wells including at least one nucleic acid extraction well having at least one nucleic acid extraction reagent sealed therein in advance;
a nucleic acid amplification/determination well for amplifying the nucleic acids and determining the amplified nucleic acids; and
one or a plurality of reagent containers having a plurality of nucleic acid extraction reagents sealed therein in advance,
wherein the one or the plurality of reagent containers and the nucleic acid amplification/determination well are linearly arranged with respect to the base member, and
the nucleic acid amplification/determination well is fitted into the base member without being tightly fixed thereto.

(Aspect 17)
The cartridge for nucleic acid detection according to Aspect 16, wherein the nucleic acid amplification/determination well is fitted into the base member with freedom in the vertical and/or horizontal direction.

(Aspect 18)
The cartridge for nucleic acid detection according to either one of Aspects 16 and 17, wherein: the nucleic acid amplification/determination well is provided with a cylindrical part; the base member is provided with a first opening; and the cylindrical part is fitted into the first opening, by which movement between the nucleic acid amplification/determination well and the base member is limited in the horizontal direction.

(Aspect 19)
The cartridge for nucleic acid detection according to Aspect 18, wherein the outer diameter of the cylindrical part of the nucleic acid amplification/determination well is made smaller than the diameter of the first opening of the base member.

(Aspect 20)
The cartridge for nucleic acid detection according to Aspect 19, wherein the outer diameter of the cylindrical part is made smaller than the diameter of the first opening by about 0.1 to about 2.0%.

(Aspect 21)
The cartridge for nucleic acid detection according to any one of Aspects 16-20, wherein: the nucleic acid amplification/determination well is provided with a plurality of nails or a plurality of recessed parts and a flange; and the base member around the first opening is sandwiched between the plurality of nails or the plurality of recessed parts and the flange, by which movement between the nucleic acid amplification/determination well and the base member is limited in the vertical direction.

(Aspect 22)
The cartridge for nucleic acid detection according to Aspect 21, wherein the distance between the plurality of nails or the plurality of recessed parts and the flange is made greater than the thickness of the base member around the first opening.

(Aspect 23)
The cartridge for nucleic acid detection according to Aspect 22, wherein the thickness of the base member around the first opening is made smaller with respect to the distance between the nails and the flange by about 0.1 to about 2.0%.

(Aspect 24)
The cartridge for nucleic acid detection according to any one of Aspects 16-23, wherein the one or the plurality of reagent containers are fitted into the base member.

(Aspect 25)
The cartridge for nucleic acid detection according to any one of Aspects 1-24, wherein the nucleic acid amplification/determination well is formed of a material with high light reflection efficiency.

(Aspect 26)
The cartridge for nucleic acid detection according to Aspect 25, wherein the material with high light reflection efficiency is a white resin material.

(Aspect 27)
A cartridge housing for housing the cartridges for nucleic acid detection according to any one of Aspects 1-26 in a stack.

(Aspect 28)
The cartridge housing according to Aspect 27, comprising an opening for pushing out the bottommost cartridge for nucleic acid detection.

Effect of the Invention

The present invention can provide a cartridge for nucleic acid detection whose structure can be altered according to the characteristics of the reagents and the requirements such as the conditions employed for determination.

MODES FOR CARRYING OUT INVENTION

Figure 1:
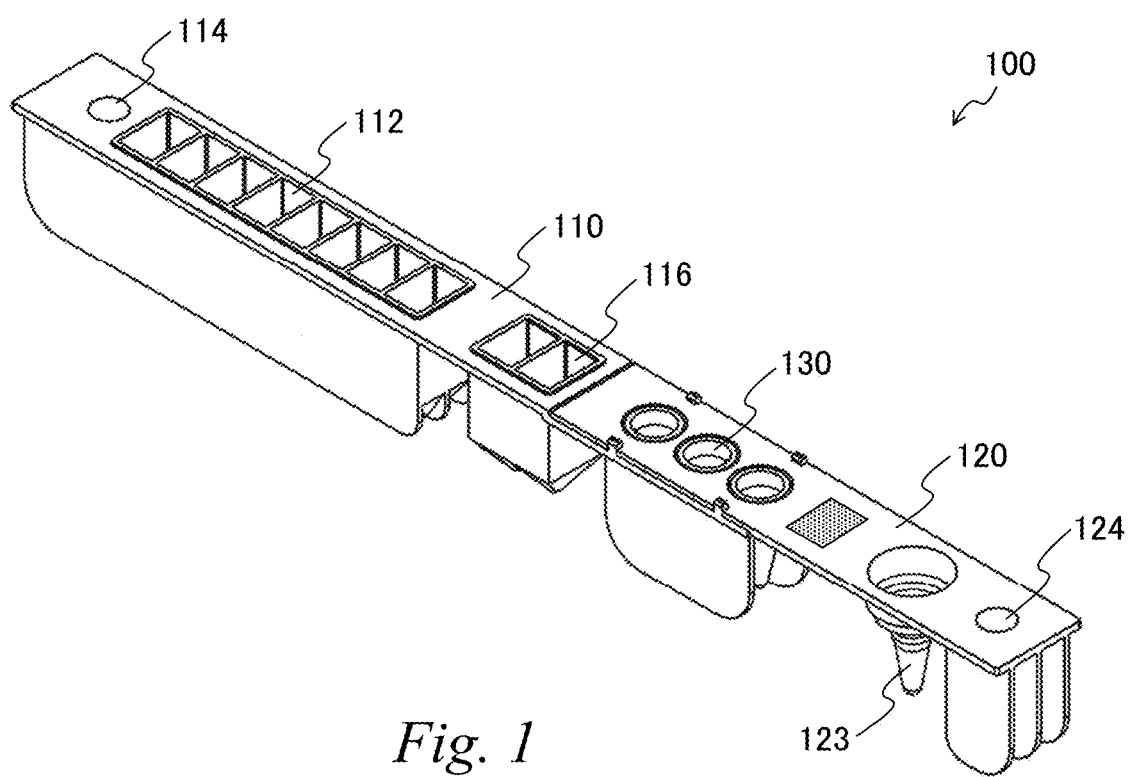
FIG. 1 A perspective view of a cartridge for nucleic acid detection according to a first embodiment of the present invention.

Cartridges for nucleic acid detection according to the embodiments of the present invention will be described with reference to the drawings. In the drawings, like components are denoted by like reference numerals. The cartridge for nucleic acid detection according to each embodiment can be used by being loaded on a nucleic acid extraction/amplification/detection apparatus.

First Embodiment

Figure 2:
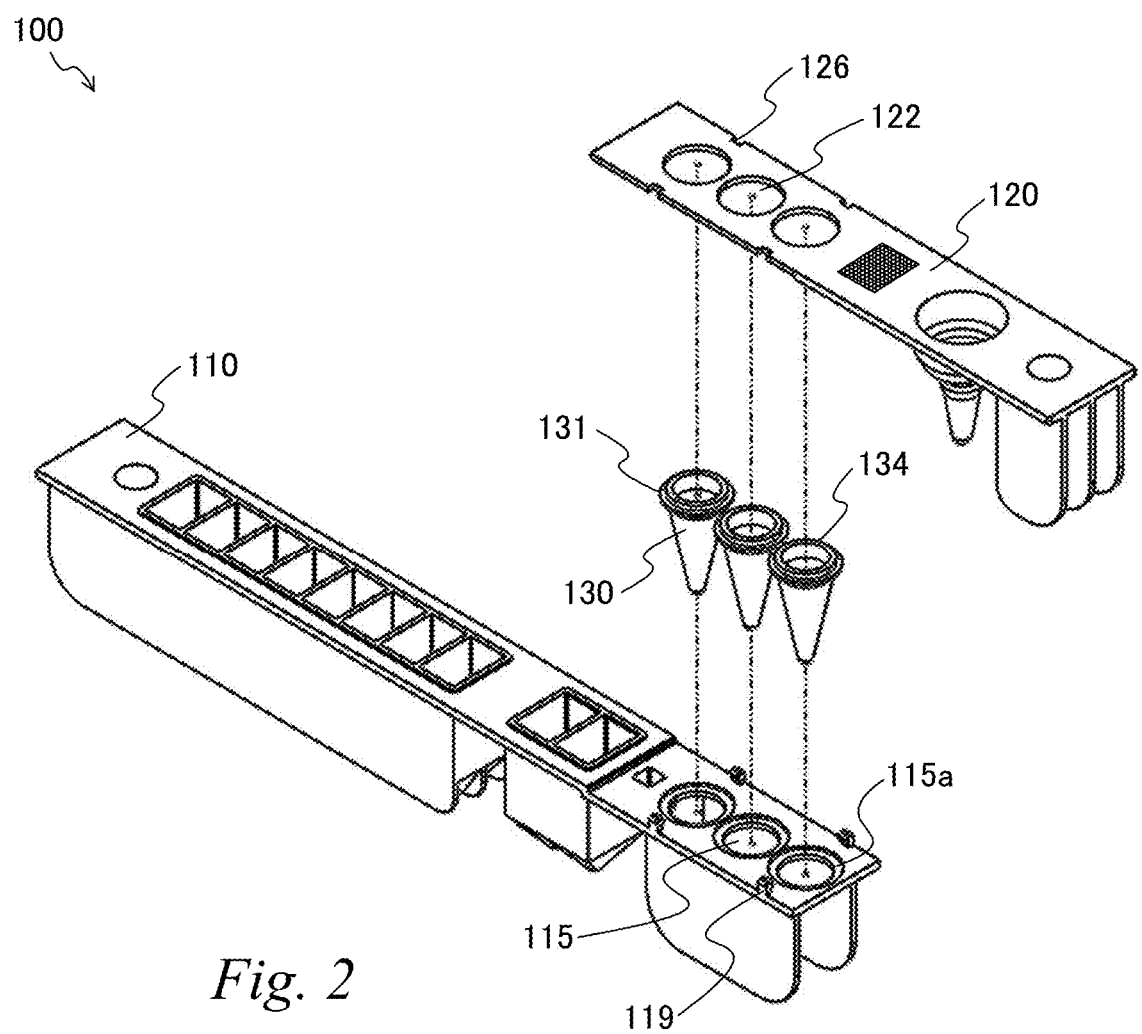
FIG. 2 An exploded perspective view of the cartridge for nucleic acid detection shown in FIG. 1.

A cartridge 100 for nucleic acid detection according to a first embodiment will be described with reference to FIGS. 1 and 2. The cartridge 100 for nucleic acid detection comprises a first member 110, a second member 120, and one or a plurality of reagent containers 130 sandwiched between and fixed to the first member 110 and the second member 120. The cartridge 100 for nucleic acid detection has a long narrow shape as a whole, with a first suction part 114 (hollow) and a second suction part 124 (hollow). The first suction part 114 and the second suction part 124 can be suctioned by a cartridge picker 540 that will be described later. The first suction part 114 and the second suction part 124 are arranged at a distance in the longitudinal direction of the cartridge 100 for nucleic acid detection. Preferably, but without limitation, the first suction part 114 is provided at one end of the cartridge 100 for nucleic acid detection while the second suction part 124 is provided at the other end of the cartridge 100 for nucleic acid detection.

Figure 3:
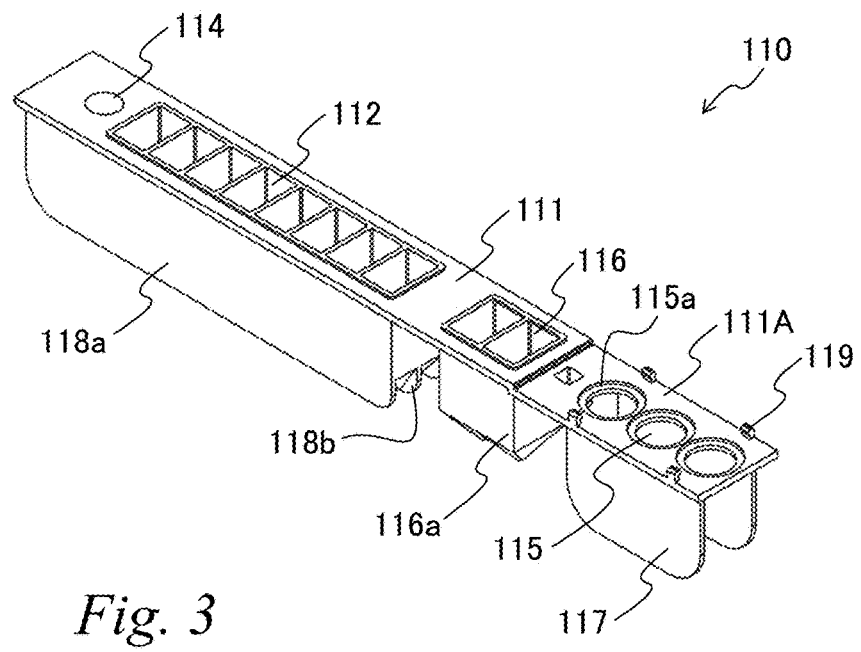
FIG. 3 A perspective view of a first member shown in FIG. 2.

The first member (base member) 110 will be described with reference to FIG. 3. The first member 110 is provided with a plate-like first top plate 111, an attachment plate 111A arranged lower than the first top plate 111, a plurality of nucleic acid extraction wells 112 open to the first top plate 111, the first suction part 114 provided at the end of the first top plate 111, a plurality of heating wells 116 open to the first top plate 111, a plurality of first openings 115 formed in the attachment plate 111A so as to accommodate the plurality of reagent containers 130, and a plurality of nails 119 projecting upward from the periphery of the attachment plate 111A.

The plurality of nucleic acid extraction wells 112 include wells that store sealed reagents. The plurality of nucleic acid extraction wells 112 preferably include wells that have at least one of a lyophilized lysis buffer, magnetic particles capable of adsorbing nucleic acids and a wash buffer sealed therein. An aluminum seal is preferably used to seal the well. The aluminum seal can be pierced with a piercer provided on a dispenser nozzle. The plurality of heating wells 116 can be heated by a heat block to denature the extracted DNA. The openings of the nucleic acid extraction wells 112 and/or the heating wells 116 are preferably rectangular while the bottom walls of the nucleic acid extraction wells 112 and/or the heating wells 116 may downwardly form quadrangular pyramids. Alternatively, the openings of the nucleic acid extraction wells 112 and/or the heating wells 116 may be circular while the bottom walls of the nucleic acid extraction wells 112 and/or the heating wells 116 may downwardly form cones. Preferably, the first opening 115 is provided with an annular protrusion 115a that annularly protrudes from the inner surface of the first opening 115.

Ribs 118a may preferably be formed on both sides of the plurality of nucleic acid extraction wells 112 along the longitudinal direction of the first member 100. Preferably, the ribs 118a extend downward from the bottom surface of the first top plate 111. Preferably, a rib 118b may be formed between the ribs 118a in parallel along the longitudinal direction of the first member 100. Preferably, a pair of ribs 117 may be formed on both sides of the plurality of first openings 115 in parallel along the longitudinal direction of the first member 100. Preferably, the ribs 117 extend downward from the bottom surface of the attachment plate 111.

Figure 4:
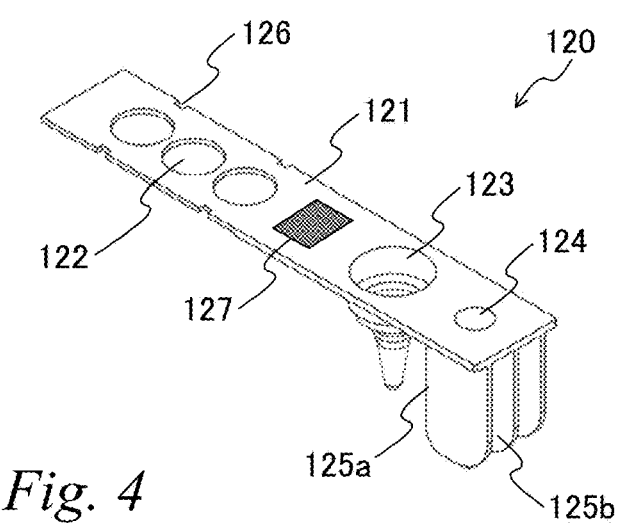
FIG. 4 A perspective view of a second member shown in FIG. 2.

The second member 120 will be described with reference to FIG. 4. The second member 120 is provided with a long narrow second top plate 121, second openings 122 open to the second top plate 121, an information recorder 127 deposited on the second top plate 121, a nucleic acid amplification/determination well 123 for amplifying and determining the extracted nucleic acids, the second suction part 124, and a plurality of notches or recessed parts 126 formed in the perimeter of the attachment plate 121. The information recorder 127 may preferably be a barcode, a QR code (registered trademark) or an IC tag. Ribs 125a may preferably be formed on both sides of the second suction part 124 in parallel along the longitudinal direction of the second member 120. Preferably, the ribs 125a extend downward from the bottom surface of the attachment plate 121. Preferably, a rib 125b may be formed between the ribs 125a in parallel along the longitudinal direction of the second member 120. The nucleic acid amplification/determination well 123 accommodates the extracted nucleic acids. The extracted nucleic acids are subjected to real-time PCR in the nucleic acid amplification/determination well 123. A thermal cycler is arranged around the nucleic acid amplification/determination well 123 so that the thermal cycler can repeat heating and cooling at predetermined temperatures for PCR.

In order to determine the nucleic acids upon real-time PCR, trigger light (excitation light) is radiated above the opening of the nucleic acid amplification/determination well 123, whereby a fluorescent substance emits fluorescence light relative to the quantity of the nucleic acids to be determined. The fluorescence light can be determined above the opening of the nucleic acid amplification/determination well 123. A determination nozzle (not shown) is movably arranged above the nucleic acid amplification/determination well 123.

The determination nozzle is provided with light-emitting optical fibers for radiating trigger light to the nucleic acid amplification/determination well 123, and light-receiving optical fibers for receiving fluorescence light from the nucleic acid amplification/determination well 123. The light-emitting optical fibers are connected to a light source while the light-receiving optical fibers are connected to a photosensor. In order to enhance the efficiency of determining the fluorescence light above the nucleic acid amplification/determination well 123, the nucleic acid amplification/determination well 123 is preferably formed of a material with high fluorescence light reflection efficiency, for example, a white resin material.

Figure 5:
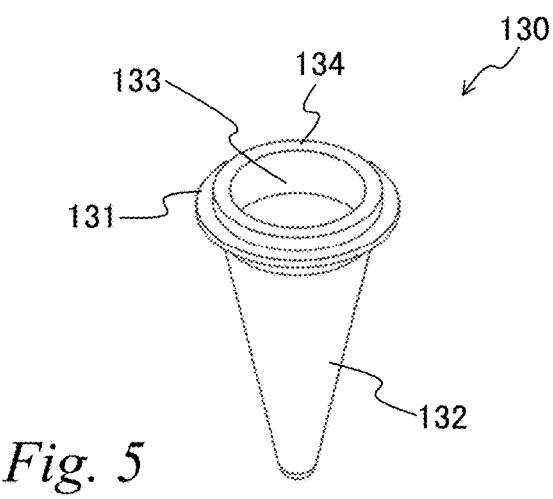
FIG. 5 A perspective view of a container shown in FIG. 2.
Figure 6:
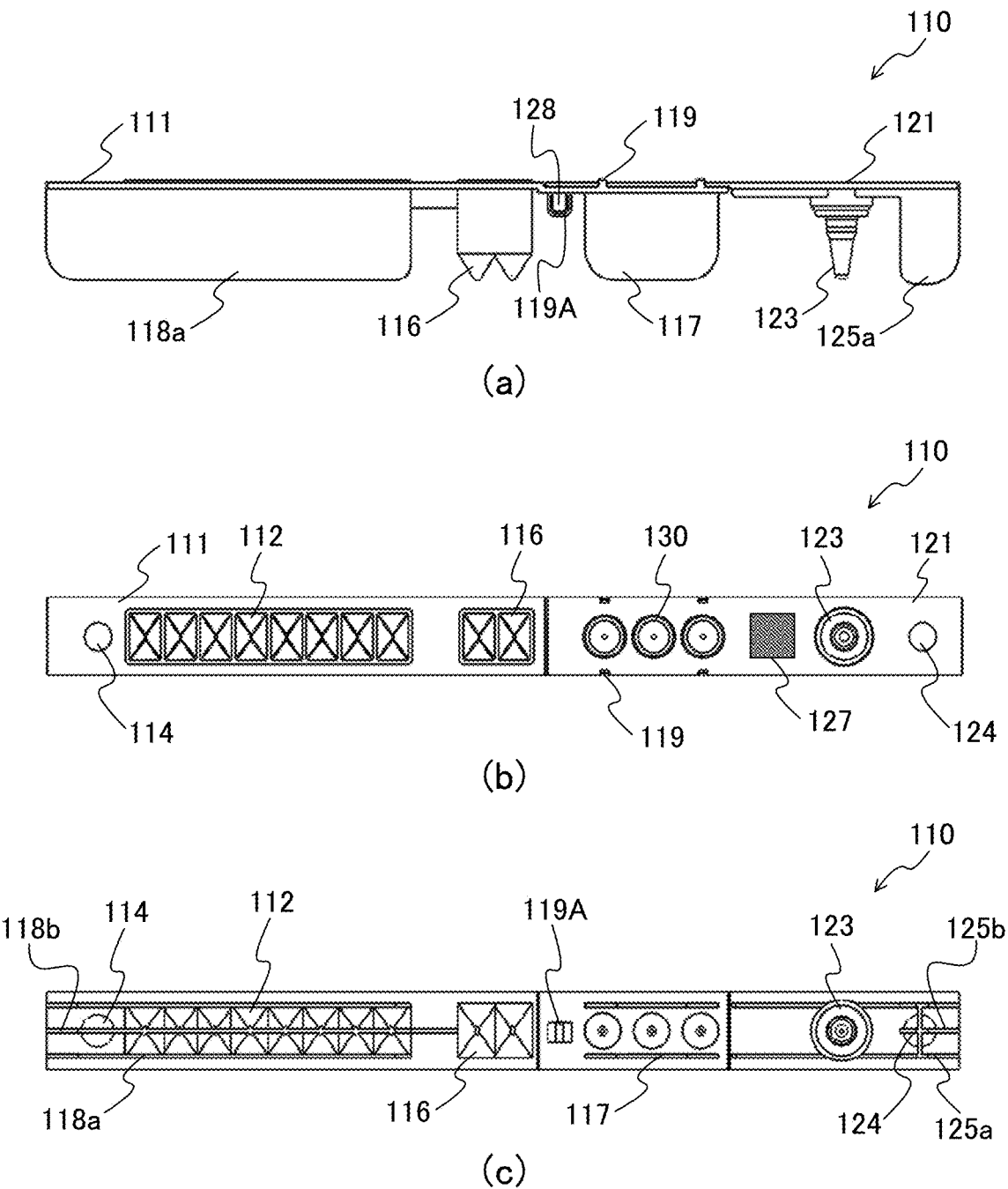
FIG. 6 (a) A side view, (b) a top view and (c) a bottom view of the cartridge for nucleic acid detection shown in FIG. 1.
Figure 7:
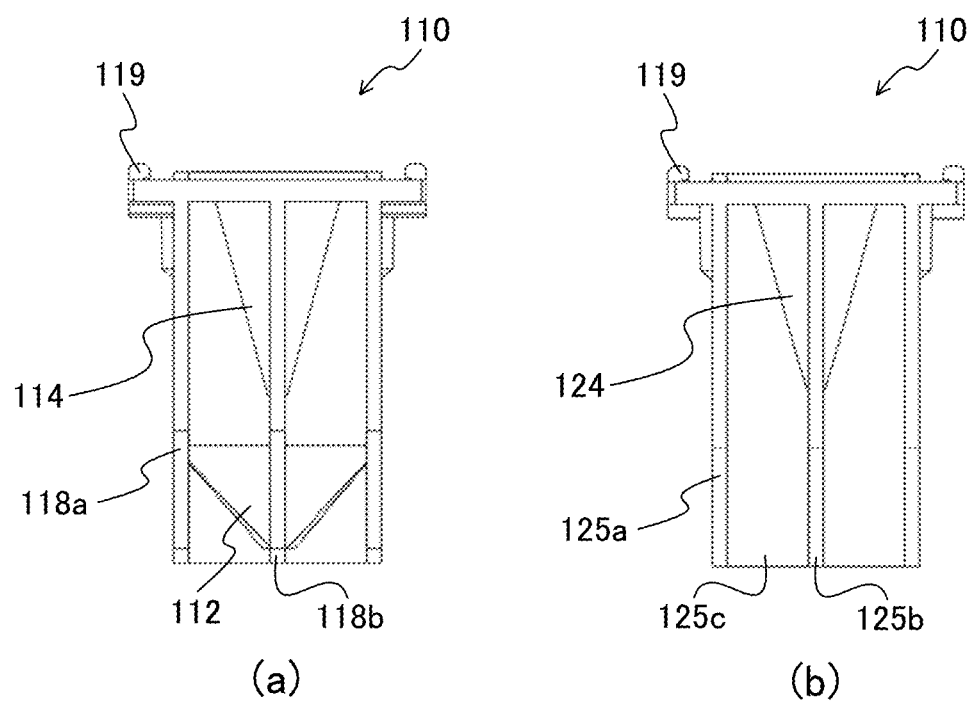
FIG. 7 (a) A view of the left end surface and (b) a view of the right end surface of the cartridge for nucleic acid detection shown in FIG. 6(1).

The reagent container 130 for storing a PCR reagent will be described with reference to FIG. 5. The reagent container 130 is provided with a circular opening 133, a flange 131 annularly protruding from the upper outer surface of the reagent container 130, a downwardly protruding conical storage wall 132, and an annular edge 134 forming the circular opening 133. According to the first embodiment, the plurality of reagent containers 130 preferably comprise, for example, three reagent containers 130 for airtightly storing the following three types of independent reagents (i)-(iii). The three types of reagents or the like may be (i) lyophilized Master Mix, (ii) a control and (iii) a lysis buffer. The Master Mix may contain, for example, a primer, DNA polymerase, dNTPs, fluorochrome and the like. The control is DNA or else that has a nucleotide sequence related to the DNA targeted for detection, which is added for confirming whether the PCR reaction is appropriately performed. The plurality of reagent containers 130 may be altered to two reagent containers 130 or four or more reagent containers 130 so as to store two or four or more types of reagents or the like according to the specification. When such an alteration is to be made, the number of the second openings 122 of the second member 120 can be altered to two or four or more without making any change to the first member 110.

With two reagent containers 130, two types of independent reagents or the like can be stored airtightly. The two types of reagents or the like may be (i) lyophilized Master Mix and (ii) a lysis buffer. This Master Mix may contain, for example, DNA polymerase, a primer, dNTPs, fluorochrome and the like.

With four reagent containers 130, four types of independent reagents or the like can be stored airtightly. The four types of reagents or the like may be (i) lyophilized Master Mix, (ii) a primer, (iii) a control and (iv) a lysis buffer. This Master Mix may contain, for example, DNA polymerase, dNTPs and fluorochrome.

In addition, instead of lyophilized Master Mix, Master Mix in a form of a liquid reagent may be enclosed in one of the reagent containers 130. Furthermore, DNA polymerase may be lyophilized and enclosed in a reagent container 130 while a lysis buffer added with a primer, dNTPs and fluorochrome (probe) may be enclosed in another reagent container 130.

The assembly of the cartridge 100 for nucleic acid detection will be described with reference to FIG. 2. Once the reagent container 130 is received by the PCR reagent container opening 115 of the first member 110, the flange 131 of the reagent container 130 sits on the annular protrusion 115a of the PCR reagent container opening 115 and fits into the PCR reagent container opening 115, whereby the reagent container 130 is mounted onto the first member 110 in a mounting state. In this mounting state, the annular edge 134 of the reagent container 130 is fitted into the second opening 122 of the second member 120 so that the plurality of nails 119 of the first member 110 fit into the plurality of notches 126 of the second member 120 and lock the second member 120, whereby the first member 110 holds the second member 120.

How the cartridge 100 for nucleic acid detection is picked up by the cartridge picker 540 will be described with reference to FIG. 8. The cartridge picker 540 is provided three-dimensionally movable above a cartridge supplying stage 500. The cartridge picker 540 is provided with a pair of suction parts (projections) 540a for suctioning the first suction part (hollow) 114 and the second suction part 124 of the cartridge 100 for nucleic acid detection, an elevating motor 540b for raising/lowering the pair of suction parts 540a, and a horizontally transferring motor 540c for transferring the cartridge picker 540 along a first rail 542 that extends in the horizontal direction.

Each of the pair of suction parts 540a projects conically with a suction port at the tip, where the suction port is connected with a vacuum pump (not shown). The cartridge 100 for nucleic acid detection is picked up by transferring the cartridge picker 540 above the cartridge 100 for nucleic acid detection and lowering the pair of suction parts 540a as indicated by the dashed line to suction the cartridge 100 for nucleic acid detection. The cartridge picker 540 suctioning the cartridge 100 for nucleic acid detection is raised to move and mount the cartridge 100 onto a treatment lane 300 where nucleic acids are to be extracted, amplified and determined.

The pair of suction parts 540a are supported by a suction part support member 540e. Preferably, the suction part support member 540e is provided with a stretching mechanism so as to alter the distance between the pair of suction parts 540 according to the cartridges having different longitudinal dimensions to allow such cartridges to be picked up. When a stretching mechanism is not provided, a plurality of suction part support members having different lengths can be provided to allow cartridges with different dimensions to be picked up. Furthermore, the cartridge picker 540 comprises a cartridge information storage medium 127 and/or an information readout unit 540e for reading out information from the container information storage medium 136.

Figure 9:
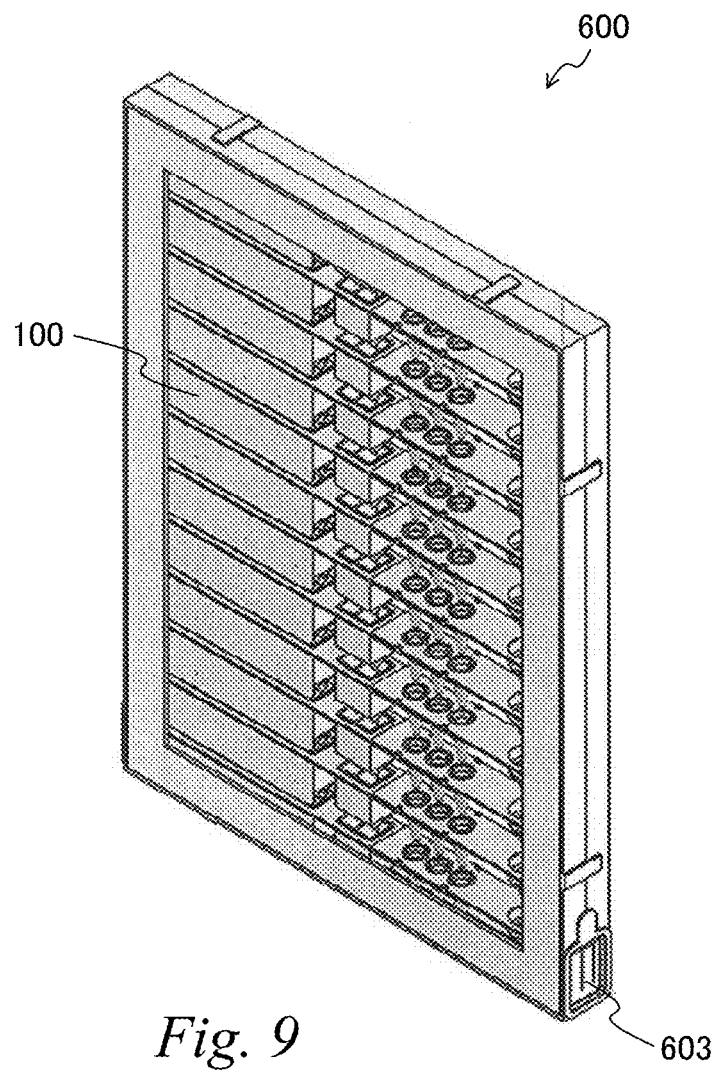
FIG. 9 A perspective view of a cartridge carton for housing the cartridges for nucleic acid detection shown in FIG. 1.
Figure 10:
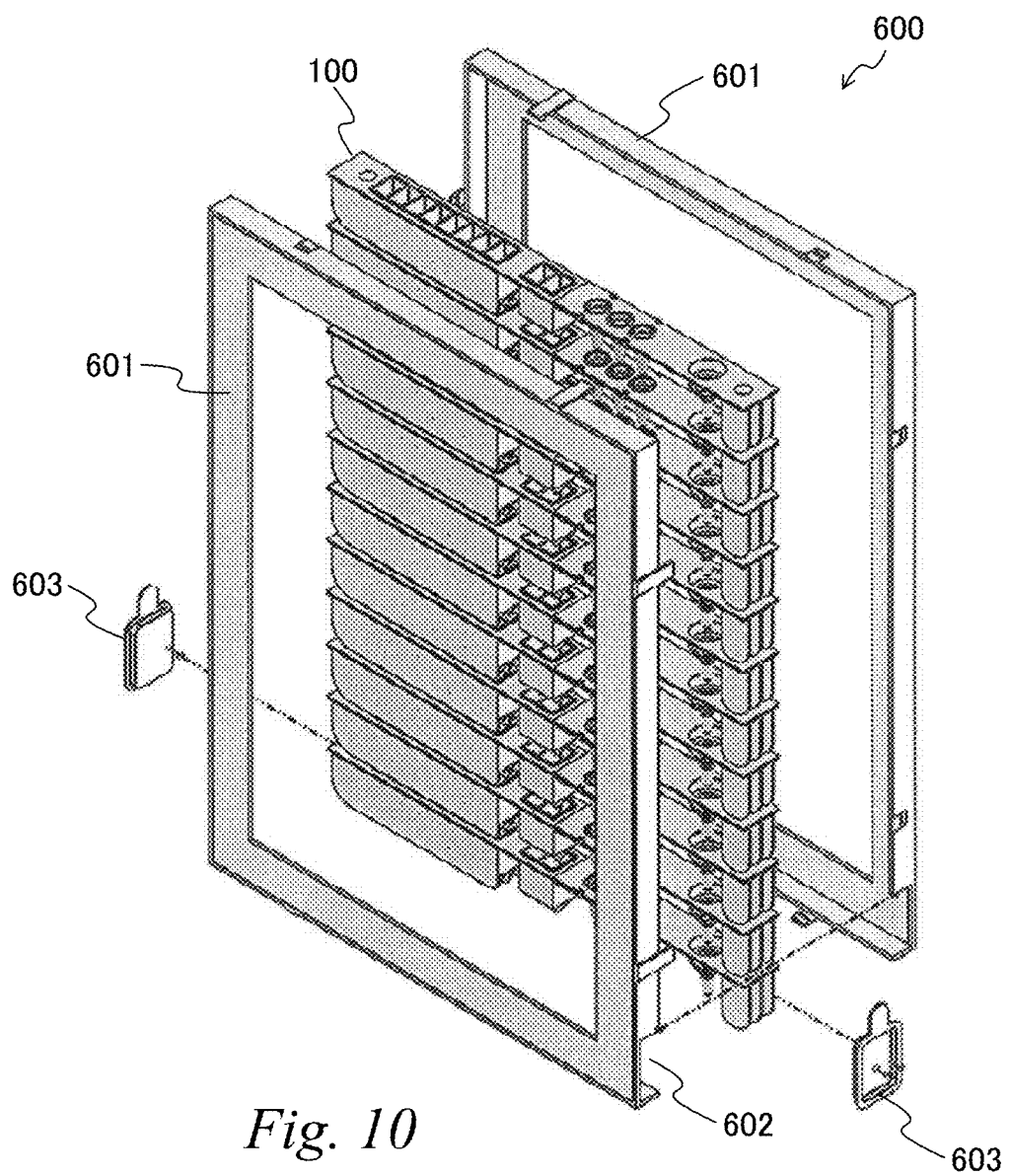
FIG. 10 An exploded perspective view of the cartridge carton shown in FIG. 9.

A cartridge carton (cartridge housing) 600 for housing a plurality of cartridges 100 for nucleic acid detection will be described with reference to FIGS. 9 and 10. The cartridge carton 600 houses the plurality of cartridges 100 for nucleic acid detection in a stack in the vertical direction. The cartridge carton 600 is provided with a pair of frames 601, an opening 602 formed at a lower part of the narrower side surface of the cartridge carton 600 and a cap 603 for closing the opening 602. While only one opening 602 is shown in FIGS. 9 and 10, there is another opening 602 at a lower part of the opposite narrower side surface. A push-out bar (not shown) is inserted into the cartridge carton 600 from one opening 602 to press and push out the bottommost cartridge 100 for nucleic acid detection from the other opening 602 onto the cartridge supplying stage 500.

Figure 11:
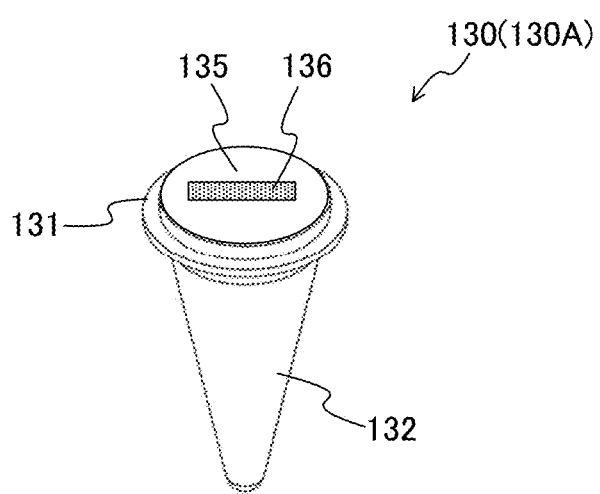
FIG. 11 A perspective view of the container shown in FIG. 5 sealed with an aluminum seal.
Figure 12:
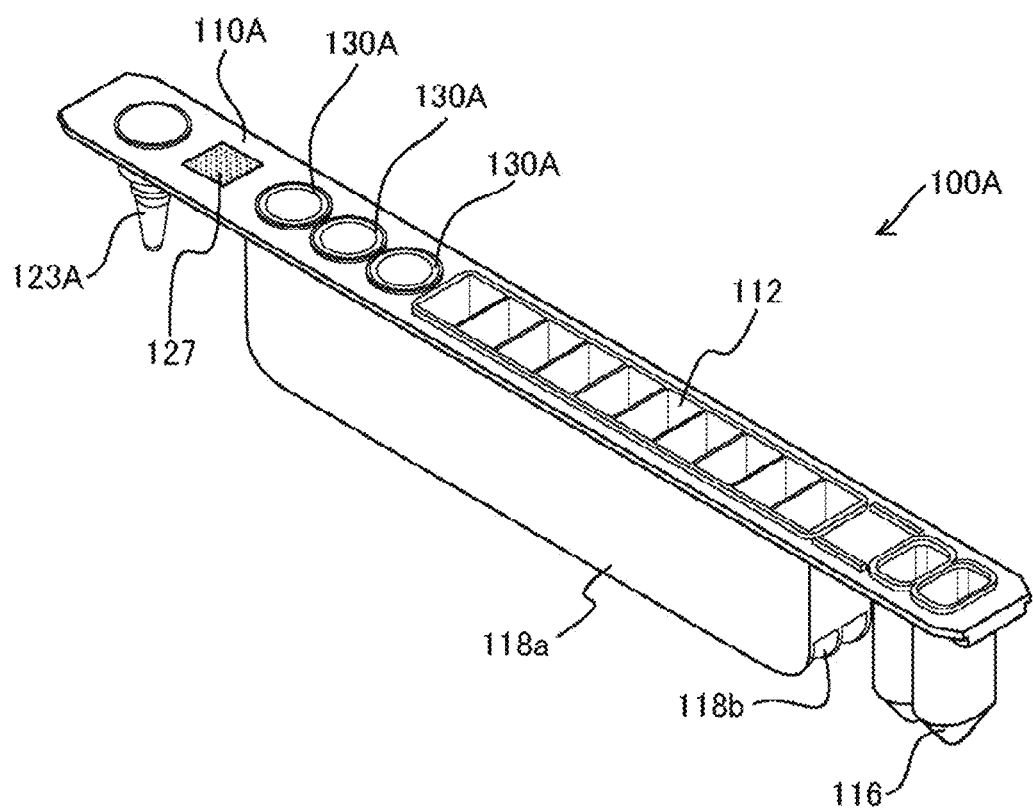
FIG. 12 A perspective view of a cartridge for nucleic acid detection according to a second embodiment of the present invention.
Figure 13:
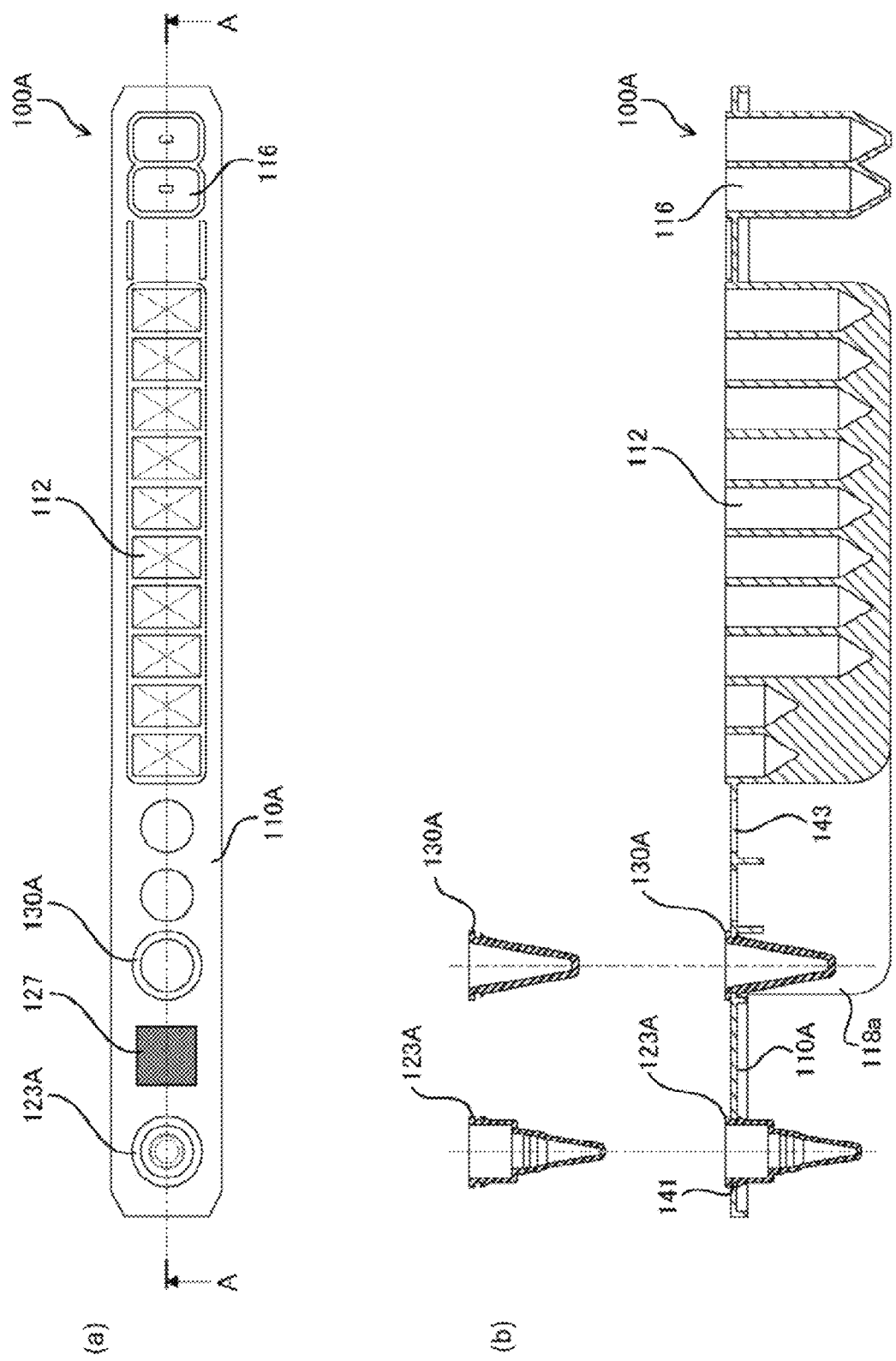
FIG. 13 (a) A top view and (b) an exploded cross-sectional view of the cartridge for nucleic acid detection shown in FIG. 12.

As can be appreciated from FIG. 11, the openings of the reagent container 130 of the first embodiment and the reagent container 130A of the second embodiment are sealed with seals (aluminum seals) 135, on which container management information 136 such as production lot is printed. Moreover, the container management information 136 may be linked with the information of the cartridge information storage medium (barcode, etc.) 127 so as to manage the reagent information more precisely.

When three separate PCR reagents or the like are loaded into the cartridge 100 for nucleic acid detection of the first embodiment, the three reagent containers 130 are prefilled with these reagents and sealed with aluminum seals. When a dispenser chip is inserted into the reagent container 130 for piercing the aluminum seal upon the reaction step, the reagent container 130 may float up. In order to prevent this floating, a structure is employed where the annular part 131 of the reagent container 130 is sandwiched and secured from top and bottom with the first member 110 and the second member 120.

Alternatively, the first member 110 (storage unit for DNA extraction reagent and the like) and the second member 120 (DNA amplification/determination unit) in the first embodiment may be integrally welded by ultrasonic heating.

In order to manage (store) the cartridge 100, 100A-D according to each embodiment at ordinary temperature, the DNA extraction reagent (lysis buffer) stored in the well 112 and polymerase stored in the reagent container 130, 130A are preferably lyophilized and sealed. In each embodiment, the well 123, 123A is preferably capped upon conducting real-time PCR.

In each embodiment, the entire reaction process, i.e., from DNA extraction to PCR determination, can be conducted on the integrated cartridge for nucleic acid detection. Furthermore, since the prefilled reagents and buffer are sealed, the user can be freed from troublesome management of them. In the first embodiment, the phrase "a plurality of containers are fixed to be a part of the first member and/or the second member" means that each of the plurality of containers is welded, adhered and/or fit to the first member and/or the second member to be a part thereof. Furthermore, according to the present invention, the phrase "the first member, the second member and the plurality of containers are integrated" means that the first member, the second member and the plurality of containers are directly or indirectly welded, adhered and/or fit to each other to form a single cartridge for nucleic acid detection.

Second Embodiment

A cartridge 100A for nucleic acid detection according to a second embodiment will be described with reference to FIGS. 12-15. As can be appreciated from FIGS. 12 and 13, the cartridge 100A for nucleic acid detection comprises a base member 110A, a nucleic acid amplification/determination well (PCR tube) 123A attached to the base member 110A and a plurality of reagent containers (reagent tubes) 130A attached to the base member 110A. The base member 110A is preferably integrated with a plurality of nucleic acid extraction wells 112 and a plurality of heating wells 116. The base member 110A is provided with a circularly opened first opening 141 for receiving the nucleic acid amplification/determination well 123A and a plurality of circularly opened second openings 143 for receiving the plurality of reagent containers 130A. The first opening 141 and the plurality of second openings 143 are arranged linearly or in a row with respect to the base member 110A. Accordingly, the plurality of reagent containers 130A and the nucleic acid amplification/determination well 123A are also arranged linearly or in a row with respect to the base member 110A.

Similar to the nucleic acid amplification/determination well 123 of the first embodiment, the nucleic acid amplification/determination well 123A accommodates the extracted nucleic acids. The extracted nucleic acids are subjected to real-time PCR in the nucleic acid amplification/determination well 123A. A thermal cycler is arranged around the nucleic acid amplification/determination well 123A so that the thermal cycler can repeat heating and cooling at predetermined temperatures for PCR.

Figure 14:
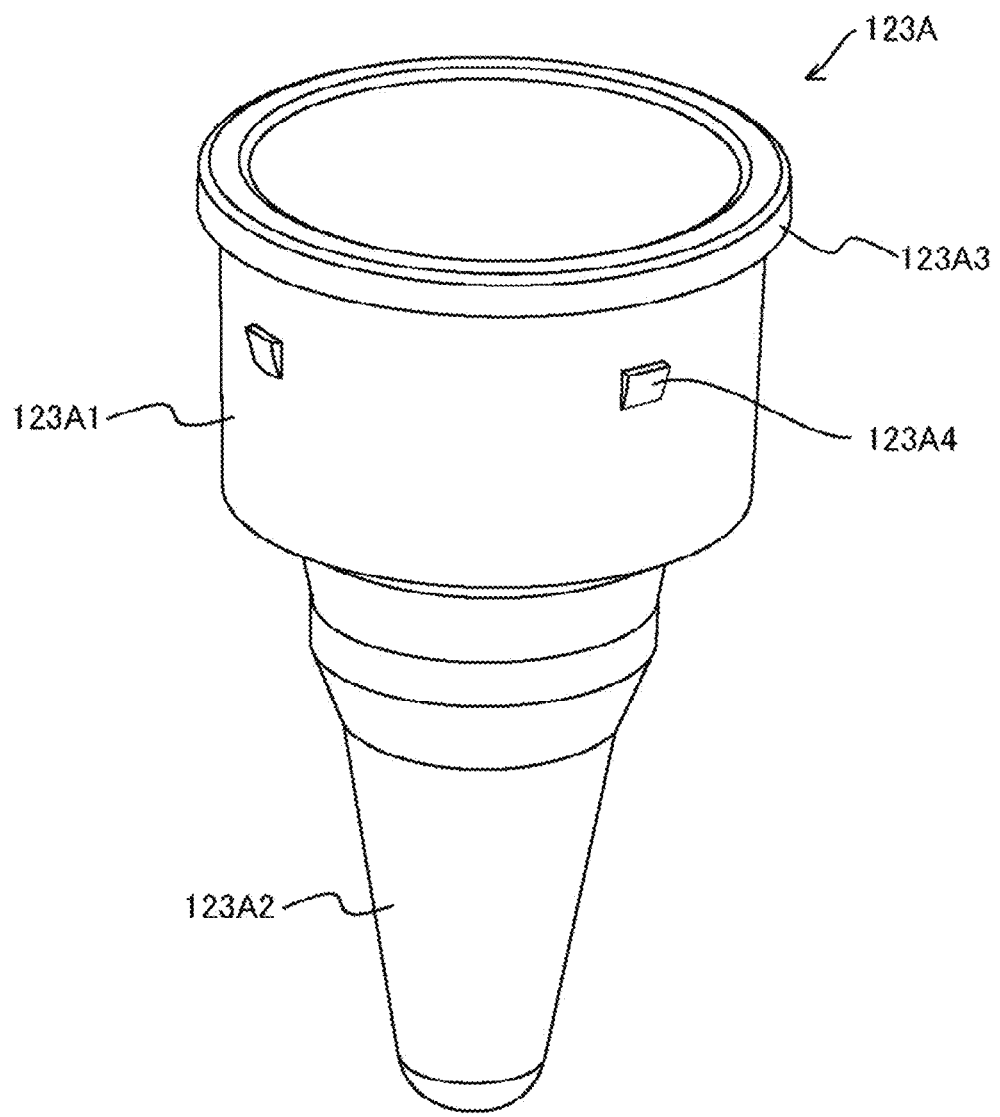
FIG. 14 A perspective view of a nucleic acid amplification/determination well used in the cartridge for nucleic acid detection shown in FIG. 12.

As can be appreciated from FIG. 14, the nucleic acid amplification/determination well 123A comprises a cylindrical part 123A1 for receiving a cap (not shown) for sealing the upper surface opening, a storage part 123A2 formed below the cylindrical part 123A1 for accommodating the extracted nucleic acid solution, a plurality of nails 123A4 formed on the outer surface of the cylindrical part 123A1 and a flange 123A3 formed at the upper edge of the cylindrical part 123A1. Similar to the nucleic acid amplification/determination well 123, the nucleic acid amplification/determination well 123A may be formed of a material with high reflection efficiency, for example, a white resin material.

The cylindrical part 123A1 of the nucleic acid amplification/determination well 123A is preferably fitted into the first opening 141 of the base member 110A without being tightly fixed thereto.

More specifically, the cylindrical part 123A1 of the nucleic acid amplification/determination well 123A is preferably fitted into the first opening 141 of the base member 110A with freedom in the horizontal direction. In other words, the cylindrical part 123A1 of the nucleic acid amplification/determination well 123A is preferably fitted into the first opening 141 of the base member 110A but loosely in the horizontal direction. Specifically, the outer diameter of the cylindrical part 123A1 may be made smaller than the diameter of the first opening 141. Preferably, the outer diameter of the cylindrical part 123A1 may be made smaller than the diameter of the first opening 141 by about 0.1 to about 2.0%, about 0.5 to about 1.0%, about 0.1 to about 1.0% or about 0.1 to about 0.5%. Accordingly, the nucleic acid amplification/determination well 123A can be loosely fit, i.e., movably fit, into the first opening 141. Moreover, since the cylindrical part 123A1 has certain elasticity, the plurality of nails (projections) 123A4 elastically deform inward upon fitting the cylindrical part 123A1 into the first opening 141 and thus the plurality of nails 123A4 can downwardly pass through the first opening 141. Here, a plurality of recessed parts may be formed in the base member 110A around the first opening 141 so that the plurality of nails (projections) 123A4 can be fitted into the recessed parts to fit the nucleic acid amplification/determination well 123A into the first opening 141.

Moreover, the cylindrical part 123A1 of the nucleic acid amplification/determination well 123A is preferably fitted into the first opening 141 of the base member 110A with freedom in the vertical direction. In other words, the cylindrical part 123A1 of the nucleic acid amplification/determination well 123A is preferably fitted into or sandwiched by the first opening 141 of the base member 110A loosely in the vertical direction. Specifically, the distance between the upper edge surface of the nails 123A4 and the lower edge surface of the flange 123A3 may be made greater than the thickness of the base member 110A around the first opening 141. Preferably, the thickness of the base member 110A around the first opening 141 can be made smaller than the distance between the upper edge surface of the nails 123A4 and the lower edge surface of the flange 123A3 by about 0.1 to about 2.0%, about 0.5 to about 1.0%, about 0.1 to about 1.0% or about 0.1 to about 0.5%. With such a structure, the nucleic acid amplification/determination well 123A can be loosely fitted into the first opening 141 with freedom in the vertical and/or horizontal direction.

The reason why the nucleic acid amplification/determination well 123A should be freely fitted into the first opening 141 will be described. Due to manufacturing error or the like of each member, displacement may be caused between the outer surface of the well 123A and the heating/cooling surface of the thermal cycler in the vertical direction and the horizontal direction. Even in a case of such displacement, since the well 123A is loosely and movably fitted into the thermal cycler, the thermal cycler can push the well 123A to make a movement so that the outer surface of the nucleic acid amplification/determination well 123A can easily make close contact with the heating/cooling surface of the thermal cycler.

Figure 15:
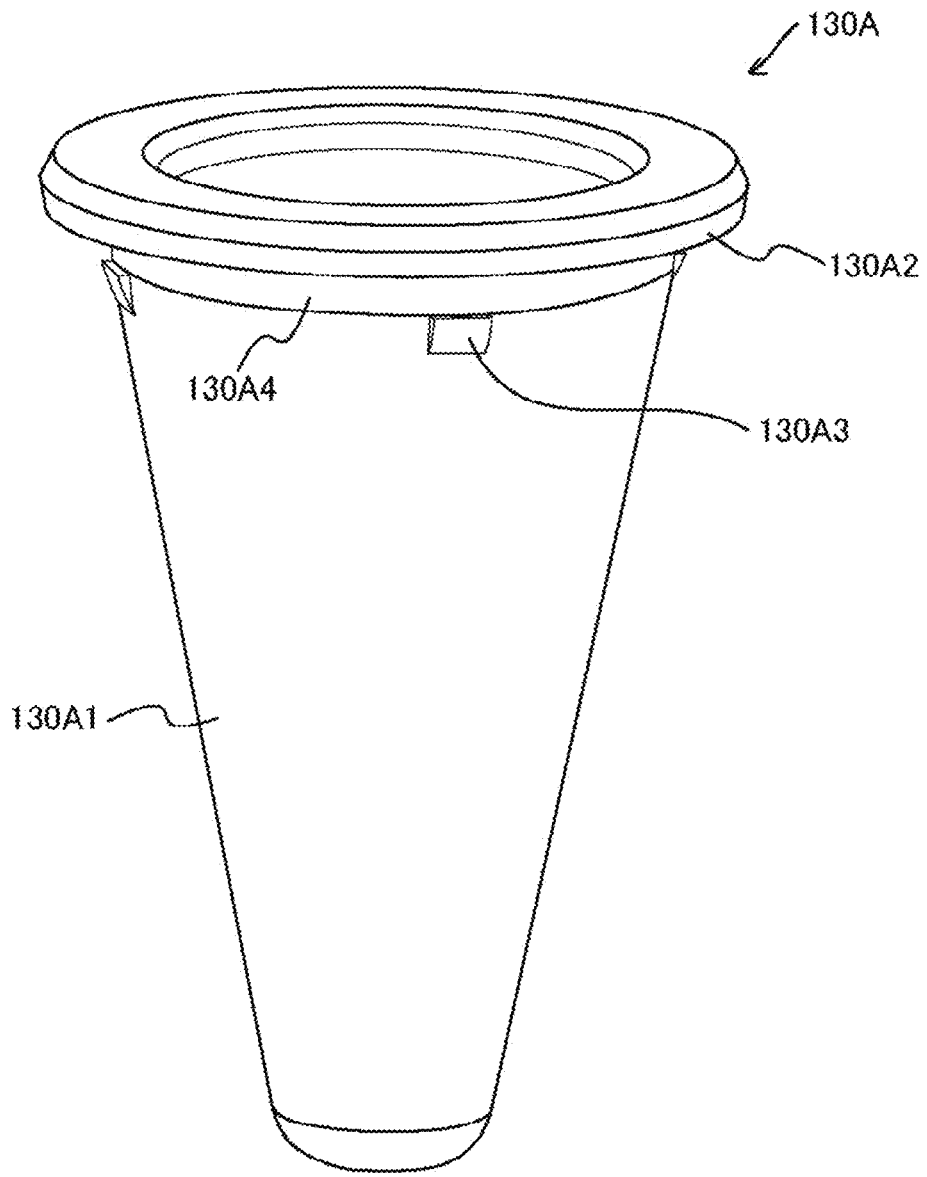
FIG. 15 A perspective view of a PCR reagent container used in the cartridge for nucleic acid detection shown in FIG. 12.

As can be appreciated from FIG. 15, the reagent container 130A comprises a storage part 130A1 for storing a PCR reagent, a flange 130A2 formed at the upper edge of the storage part 130A1, a plurality of nails (projections) 130A3 formed in the vicinity of the upper outer surface of the storage part 130A1, and a cylindrical part 130A4 formed between the flange 130A2 and the plurality of nails 130A3.

In order to perfectly fit the cylindrical part 130A4 of the reagent container 130A into the second opening 143 of the base member 110A, the outer diameter of the cylindrical part 130A4 is preferably nearly the same as the diameter of the second opening 144. As a result, the reagent container 130A is fixedly fitted into, i.e., fixed to, the second opening 143. Since the storage part 130A1 has certain elasticity, the plurality of nails 130A3 elastically deform inward upon fitting the cylindrical part 130A4 into the second opening 144 and thus the plurality of nails 130A3 can downwardly pass through the second opening 144. A plurality of recessed parts may be formed in the base member 110A around the second opening 144 so that the plurality of nails (projections) 130A3 can be fitted into the recessed parts to fit the plurality of reagent containers into the second openings 143.

Figure 16:
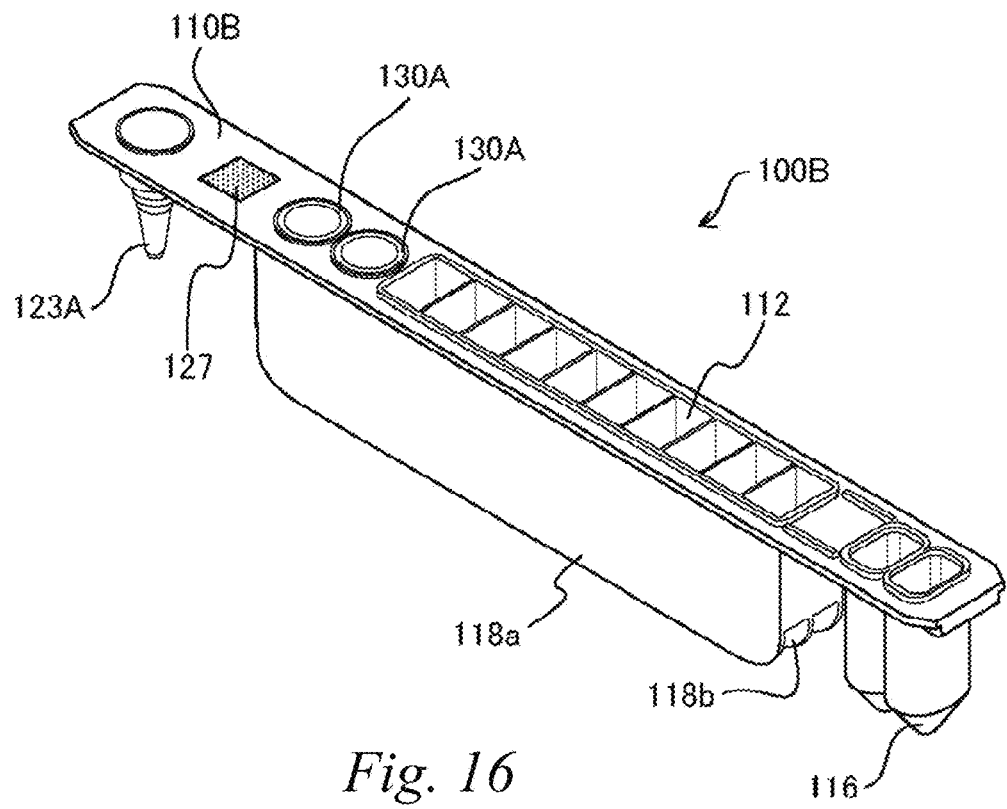
FIG. 16 A perspective view of a first variation of the cartridge for nucleic acid detection shown in FIG. 12.
Figure 17:
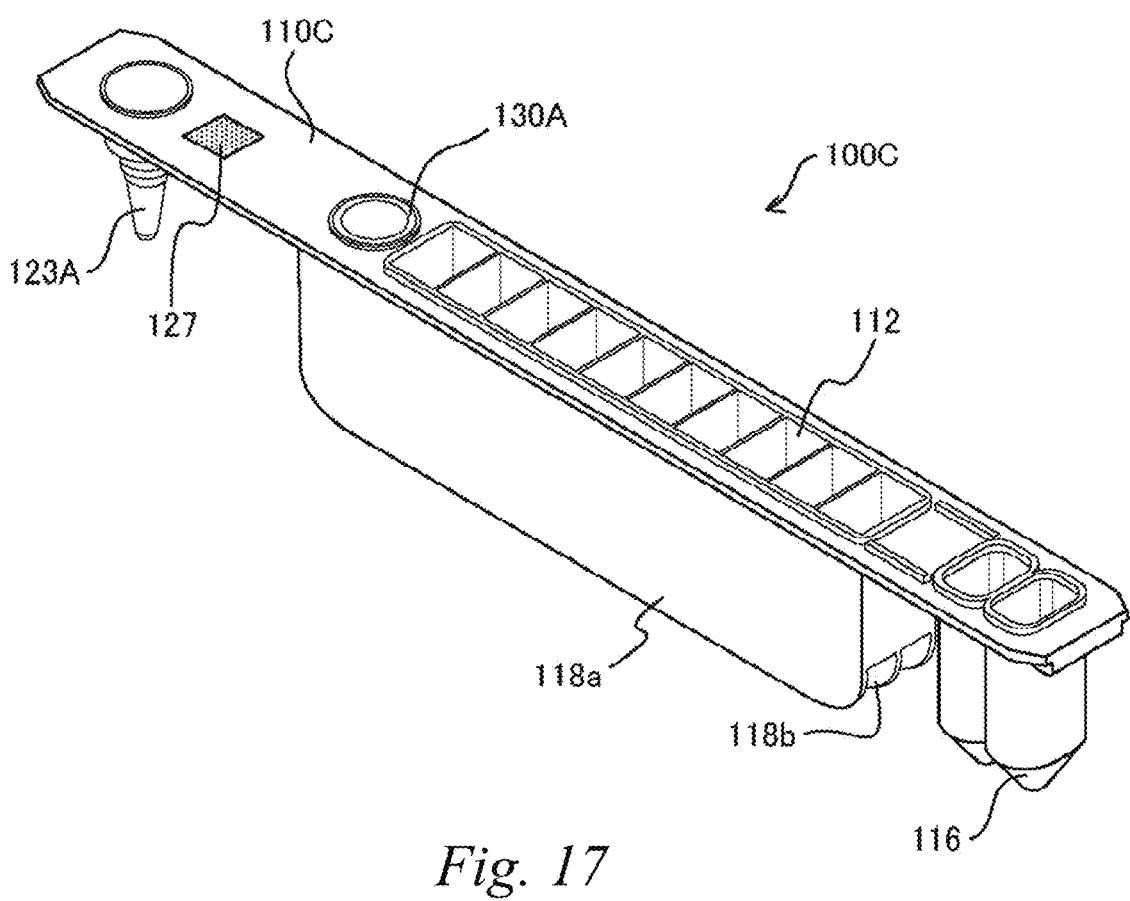
FIG. 17 A perspective view of a second variation of the cartridge for nucleic acid detection shown in FIG. 12.

Cartridges 100B and 100C for nucleic acid detection as variations of the second embodiment will be described with reference to FIGS. 16 and 17. The cartridge 100B for nucleic acid detection shown in FIG. 16 is provided with two reagent containers 130A while the cartridge 100C for nucleic acid detection shown in FIG. 17 is provided with one reagent container 130A. Other structures of the cartridges 100B and 100C for nucleic acid detection are the same as those of the cartridge 100A for nucleic acid detection.

Third Embodiment

Figure 18:
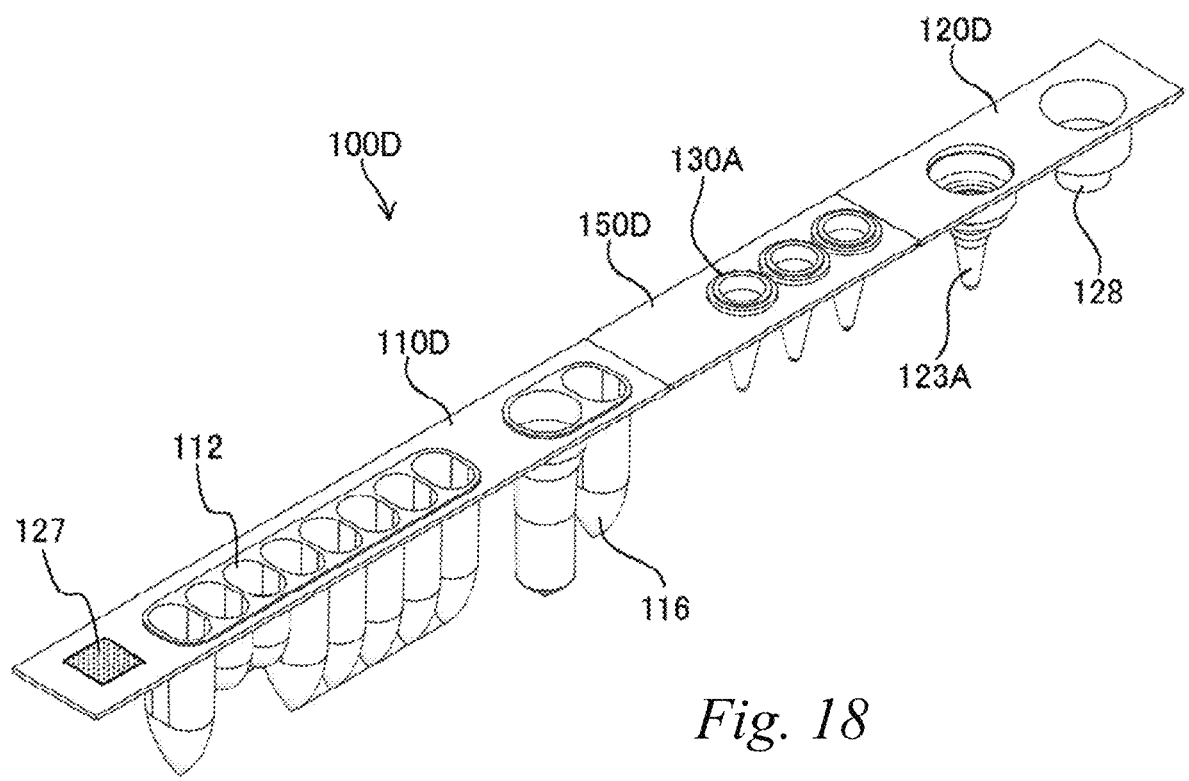
FIG. 18 A perspective view of a third variation of the cartridge for nucleic acid detection shown in FIG. 12.

A cartridge 100D for nucleic acid detection according to a third embodiment will be described with reference to FIG. 18. As can be appreciated from FIG. 18, the cartridge 100D for nucleic acid detection comprises a plate-like first member 110D, a plate-like second member 120D, and a plate-like third member 150D that is connected with the first member 110D and the second member 120D. The first member 110D is provided with a plurality of nucleic acid extraction wells 112 and a plurality of heating wells 116. The plurality of wells 112 and 116 may preferably be integrated with the first member 110D. The second member 120 is provided with a nucleic acid amplification/determination well 123A, and a cap housing 128 for housing a cap (not shown) for sealing the nucleic acid amplification/determination well 123A. The cap housing 128 is integrated with the second member 120.

Similar to the second embodiment, the nucleic acid amplification/determination well 123A may be made as a separate member from the second member 120D and loosely fitted into the opening formed in the second member 120D. The well 123A as a separate member can be formed of a white resin material. Alternatively, similar to the first embodiment, the nucleic acid amplification/determination well 123A may be integrated with the second member 120D. The second member 120 integrated with the well 123A may be formed of a white resin material.

The third member 150D is provided with a plurality of reagent containers 130A. Similar to the second embodiment, the plurality of reagent containers 130A may be made as separate members from the third member 150D and fitted into the plurality of openings formed in the third member 150D. The first member 110D and the third member 150D are connected via a fitting structure or the like provided on their bottom surfaces. Similarly, the second member 120D and the third member 150D are connected via a fitting structure or the like provided on their bottom surfaces.

Figure 8:
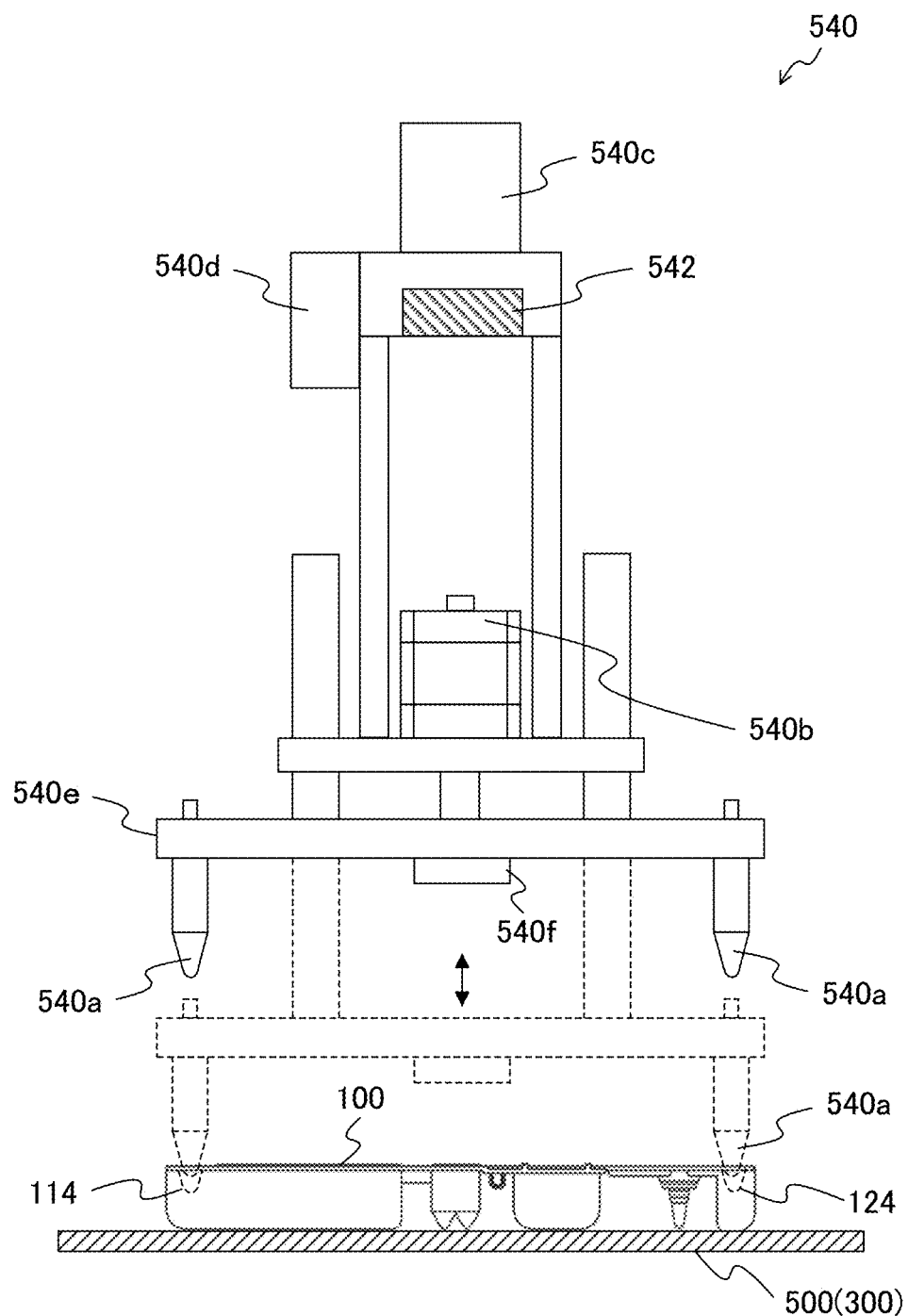
FIG. 8 A side view showing a state where the cartridge for nucleic acid detection shown in FIG. 1 is taken out with a cartridge picker.

In the second and third embodiments, each of the cartridges 100A, 100B, 100C and 100D for nucleic acid detection is provided with the first suction part (hollow) 114 and the second suction part 124 so as to be transferable by being suctioned by the cartridge picker 540 shown in FIG. 8. In the second and third embodiments, a plurality of cartridges 100A, 100B, 100C or 100D for nucleic acid detection may be stacked in the vertical direction to be housed in the cartridge carton 600 shown in FIGS. 9 and 10. In the first embodiment, the nucleic acid amplification/determination well 123 may be fitted into the second member 120 without being tightly fixed thereto (in a free state) as a separate member from the second member 120.

DESCRIPTION OF REFERENCE NUMERALS

100 Cartridge for nucleic acid detection
100A-100D Cartridges for nucleic acid detection
110 First member
111 First top plate
111A Attachment plate
112 Nucleic acid extraction well
114 First suction part
115 First opening
116 Heating well
120 Second member
121 Second top plate
122 Second opening
123 Nucleic acid amplification/determination well
123A Nucleic acid amplification/determination well
124 Second suction part
126 Notches (recessed parts)
127 Information recorder
130 Container
130A Container
131 Flange
132 Storage part
133 Circular opening
134 Annular edge
540 Cartridge picker
600 Cartridge carton (cartridge housing)

The invention claimed is:

1. A cartridge for nucleic acid detection which is used in an apparatus for extracting nucleic acids from a specimen, amplifying the extracted nucleic acids and detecting the amplified nucleic acids, the cartridge comprising:
   a first member provided with a plurality of nucleic acid extraction wells, the first member comprising at least one nucleic acid extraction well having at least one nucleic acid extraction reagent sealed therein in advance;
   a second member provided with a nucleic acid amplification/determination well for amplifying the nucleic acids and determining the amplified nucleic acids; and
   one or a plurality of reagent containers having one or a plurality of nucleic acid amplification reagents sealed therein in advance,
   wherein the one or the plurality of reagent containers are fixed so as to be a part of the first member and/or the second member, thereby integrating the first member, the second member and the plurality of reagent containers, and
   wherein the one or the plurality of reagent containers is fixed to the first member and the second member by being vertically sandwiched between the first member and the second member.

2. The cartridge for nucleic acid detection according to claim 1, wherein the plurality of nucleic acid amplification reagent containers are fitted into first openings formed in the first member and/or second openings formed in the second member.

3. The cartridge for nucleic acid detection according to claim 2, wherein:
   the first member is provided with a first top plate that has a plurality of open nucleic acid extraction wells and an attachment plate having the first openings;
   the second member is provided with a second top plate that has the second openings; and
   the second top plate is attached to the attachment plate.

4. The cartridge for nucleic acid detection according to claim 2, wherein:
   a protrusion is formed on the inner surface of the first opening or the second opening; the container is provided with a flange that protrudes out from the outer surface of the container; and the flange sits on the protrusion.

5. The cartridge for nucleic acid detection according to claim 4, wherein the protrusion is an annular protrusion; and the flange is an annular flange.

6. The cartridge for nucleic acid detection according to claim 1, wherein a plurality of recessed parts are formed in either one of the first member or the second member while a plurality of nails are formed in the other one of the first member or the second member so that the plurality of nails can lock with the plurality of recessed parts to integrate the first member, the second member and the plurality of reagent containers.

7. The cartridge for nucleic acid detection according to claim 1, wherein the first member and the second member are welded.

8. The cartridge for nucleic acid detection according to claim 1, comprising a plurality of suction parts that can be suctioned by a cartridge picker.

9. The cartridge for nucleic acid detection according to claim 8, wherein the plurality of suction parts are hollows formed in each of the first member and the second member.

10. The cartridge for nucleic acid detection according to claim 1, wherein the first member is provided with a heating well for heating and denaturing the extracted nucleic acids.

11. The cartridge for nucleic acid detection according to claim 1, wherein the one or the plurality of reagent containers are provided with an opening, a seal for sealing the opening, and a container information storage medium formed on the seal.

12. The cartridge for nucleic acid detection according to claim 1, wherein the first member is provided with a plurality of ribs along its longitudinal direction.

13. The cartridge for nucleic acid detection according to claim 1, wherein the second member is provided with a plurality of ribs along its longitudinal direction.

14. The cartridge for nucleic acid detection according to claim 1, wherein the nucleic acid amplification/determination well is fitted into the second member without being tightly fixed thereto.

15. The cartridge for nucleic acid detection according to claim 1, wherein the nucleic acid amplification/determination well is formed of a material with high light reflection efficiency.

16. The cartridge for nucleic acid detection according to claim 15, wherein the material with high light reflection efficiency is a white resin material.

17. The cartridge for nucleic acid detection according to claim 1 further comprising a cartridge housing, wherein the cartridge housing houses one or more of the cartridges for nucleic acid detection in a stack.

18. The cartridge for nucleic acid detection according to claim 17, wherein the cartridge housing comprises an opening for pushing out a bottommost cartridge for nucleic acid detection from the stack.

19. The cartridge for nucleic acid detection according to claim 1, wherein the nucleic acid amplification/determination well is fitted into the second member without being tightly fixed thereto in a free state as a separate member from the second member.

* * * * *